United States Patent [19]

Remy

[11] Patent Number: 4,591,587

[45] Date of Patent: May 27, 1986

[54] CYCLOPROPYL PYRIDINE COMPOUNDS USEFUL AS CALCIUM CHANNEL BLOCKERS

[75] Inventor: David C. Remy, North Wales, Pa.

[73] Assignee: Merck & Co., Inc., Rahway, N.J.

[21] Appl. No.: 655,786

[22] Filed: Oct. 1, 1984

[51] Int. Cl.⁴ .................. A61K 31/44; A61K 31/47; C07D 221/18; C07D 221/22
[52] U.S. Cl. .................. 514/222; 514/236; 514/253; 514/280; 514/284; 544/61; 544/125; 544/361; 546/42; 546/48; 546/75
[58] Field of Search ............. 546/42, 48, 75; 544/61, 544/125, 361; 514/222, 236, 253, 280, 284

[56] References Cited

U.S. PATENT DOCUMENTS

| | | |
|---|---|---|
| 3,466,288 | 9/1969 | Hansen et al. .................. 546/74 X |
| 3,518,271 | 6/1970 | Shavel, Jr. et al. .................. 546/43 |
| 4,172,201 | 10/1979 | Jarque et al. .................. 546/63 |
| 4,178,450 | 12/1979 | Jarque et al. .................. 546/63 |

OTHER PUBLICATIONS

Bossert, et al., Angew. Chem. Int. Ed., vol. 20, pp. 762–769 (1981).
Schramm, et al., Nature, vol. 309, pp. 535–537, (Jun. 9, 1983).

*Primary Examiner*—Donald G. Daus
*Assistant Examiner*—Diana G. Rivers
*Attorney, Agent, or Firm*—Alice O. Robertson; Joseph F. DiPrima; Michael C. Sudol

[57] ABSTRACT

Novel cyclopropyl pyridine compounds useful as calcium channel blockers, pharmaceutical compositions thereof, and methods of treatment are disclosed.

9 Claims, No Drawings

CYCLOPROPYL PYRIDINE COMPOUNDS USEFUL AS CALCIUM CHANNEL BLOCKERS

BACKGROUND OF THE INVENTION

Substituted dihydropyridines are known to be useful for reducing blood pressure, effecting dilation of the coronary vessels, and preventing urospasms. Typical of such substituted dihydropyridines are those disclosed in U.S. Pat. Nos. 3,923,818; 3,905,970; 4,044,141; 4,237,137; and 4,285,955. The substituted dihydropyridines disclosed in these patents do not include fused cyclopropyl ring structures.

SUMMARY OF THE INVENTION

This invention is directed to novel cyclopropyl pyridine compounds and derivatives thereof. This invention is also directed to pharmaceutical compositions and methods of treatment for cardiovascular disorders.

DETAILED DESCRIPTION OF THE INVENTION

The specific cyclopropyl pyridine compounds of this invention are represented by the following general structural formula (I):

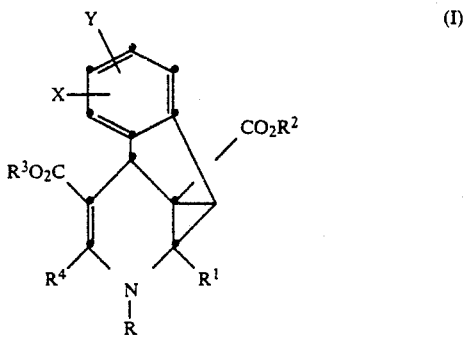

wherein:

R is hydrogen, $C_1$-$C_8$ alkyl, benzyl or $C_1$-$C_4$ carboalkoxy;

$R^1$ and $R^4$ independently are hydrogen, $C_1$-$C_8$ alkyl, $C_2$-$C_8$ alkenyl, $C_3$-$C_8$ cycloalkyl or $C_1$-$C_8$ hydroxyalkyl;

$R^2$ and $R^3$ independently are $C_1$-$C_8$ alkyl, $C_2$-$C_8$ alkenyl, $C_3$-$C_8$ cycloalkyl, $C_1$-$C_8$ hydroxyalkyl, $C_1$-$C_8$ dihydroxyalkyl, $C_2$-$C_8$ alkoxyalkyl, $C_3$-$C_8$ alkoxy(alkoxyalkyl) or $C_1$-$C_8$ aminoalkyl wherein the amino group is $NR^5R^6$ in which $R^5$ and $R^6$ independently are hydrogen, $C_1$-$C_8$ alkyl, $C_7$-$C_{14}$ phenylalkyl or $R^5$ and $R^6$ together with the N atom form a 5 or 6 membered heterocycle selected from the group consisting of piperidinyl, morpholinyl, thiomorpholinyl, pyrrolidinyl, piperazinyl or N'-$C_1$-$C_4$-alkylpiperazinyl; and X and Y independently are hydrogen, $C_1$-$C_8$ alkyl, $C_1$-$C_8$ alkoxy, $CF_3$, cyano, nitro or halo, (i.e. fluoro, chloro or bromo) or X and Y together with the phenyl group to which they are attached form a naphthyl or benzoxadiazole group, and pharmaceutically acceptable salts thereof.

The preferred compounds of this invention are those represented by the general structural formula (I) wherein:

R is hydrogen, $C_1$-$C_8$ alkyl or $C_1$-$C_4$ carboalkoxy;

$R^1$ and $R^4$ independently are hydrogen or $C_1$-$C_8$ alkyl;

$R^2$ and $R^3$ independently are $C_1$-$C_8$ alkyl or $C_1$-$C_8$ aminoalkyl wherein the amino group is $NR^5R^6$ in which $R^5$ and $R^6$ independently are hydrogen, $C_1$-$C_8$ alkyl or $C_7$-$C_{14}$ phenylalkyl; and X and Y independently are hydrogen, $C_1$-$C_8$ alkyl, $C_1$-$C_8$ alkoxy, $CF_3$, cyano, nitro or halo.

The most preferred compounds of this invention are those preferred compounds wherein: R is hydrogen; $R^1$, $R^2$, $R^3$ and $R^4$ independently are $C_1$-$C_8$ alkyl and X and Y independently are hydrogen, nitro or $C_1$-$C_8$ alkoxy and are in the 8- and 9-positions respectively.

The compounds of this invention possess asymmetric centers and thus exist in different isomeric forms. All such forms are included within the scope of this invention. Specifically, the compounds have an asymmetric center at the carbon atom to which the ester moiety, —$CO_2R^2$, is attached. Whenever that ester moiety is below the plane of the piperidine ring (i.e. down) that stereochemical configuration is denoted as the alpha ($\alpha$)-isomer. Similarly, whenever that ester moiety is above the plane of the piperidine ring (i.e. up) that stereochemical configuration is denoted as the beta ($\beta$)-isomer.

Illustrative of the compounds of this invention are the following compounds of the formula (I) which are the $\alpha$-isomer, the $\beta$-isomer or mixtures thereof:

(1) Dimethyl 1,2,3,6$\alpha$-tetrahydro-2,4-dimethyl-1,2,6-metheno-3-benzazocine-5,11$\alpha$-dicarboxylate [Formula (I) where R is hydrogen, $R^1$, $R^2$, $R^3$ and $R^4$ are methyl and X and Y are hydrogen];

(2) Dimethyl 1,2,3,6$\alpha$-tetrahydro-2,4-dimethyl-1,2,6-metheno-9-methoxy-3-benzazocine-5,11$\alpha$-dicarboxylate [Formula (I) where R is hydrogen, $R^1$, $R^2$, $R^3$ and $R^4$ are methyl, X is hydrogen and Y is 9-methoxy];

(3) Dimethyl 1,2,3,6$\alpha$-tetrahydro-2,4-dimethyl-1,2,6-metheno-8-nitro-3-benzazocine-5,11$\alpha$-dicarboxylate [Formula (I) where R is hydrogen, $R^1$, $R^2$, $R^3$ and $R^4$ are methyl, X is 8-nitro and Y is hydrogen]; and (4) Trimethyl 1,2,3,6$\alpha$-tetrahydro-2,4-dimethyl-1,2,6-metheno-3-benzazocine-3,5,11$\alpha$-tricarboxylate [Formula (I) where R is carbomethoxy, $R^1$, $R^2$, $R^3$ and $R^4$ are methyl and X and Y are hydrogen].

The pharmaceutically acceptable salts are those acid addition salts of non-toxic, pharmaceutically acceptable acids and include salts of inorganic acids such as hydrochloric, hydrobromic, hydroiodic, phosphoric, sulfuric, nitric and the like, and organic acids such as trifluoroacetic and trichloroacetic and the like and include acids related to the pharmaceutically acceptable salts listed in Journal of Pharmaceutical Science, 66, 2 (1977) and incorporated herein by reference.

The compounds of this invention are conveniently prepared from known or readily obtainable starting materials utilizing the general synthetic pathway described below which is also disclosed and claimed in co-pending patent application Attorney Docket Number 17169 filed contemperaneously herewith: Ser. No. 655,785

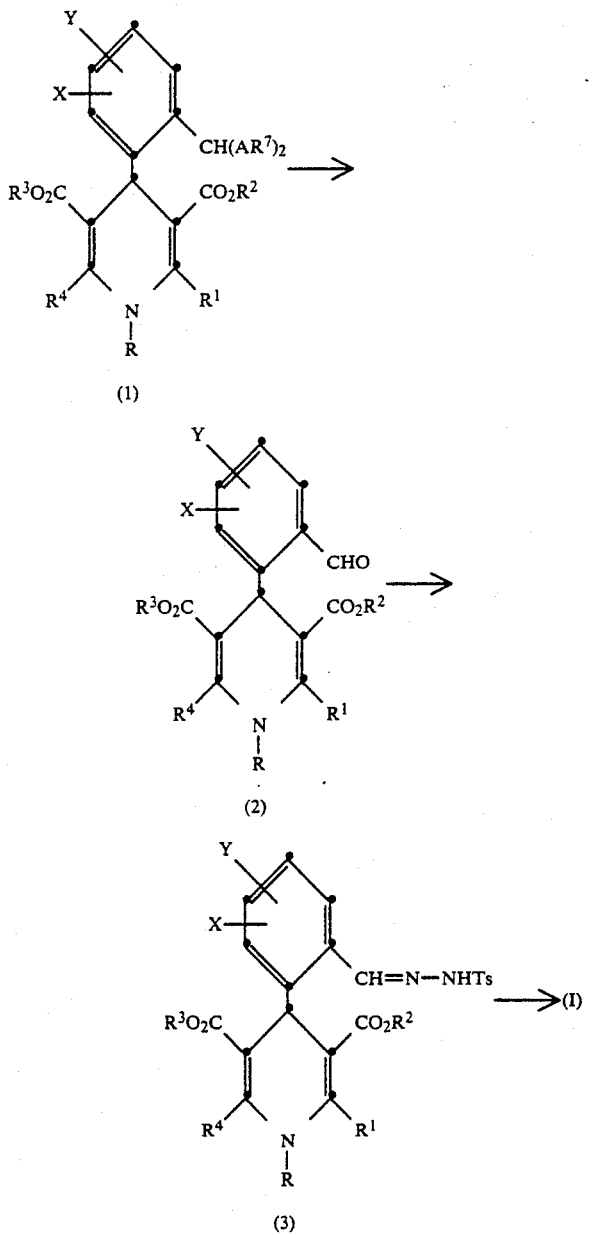

The aryl dihydropyridine (1) wherein $R^1$, $R^2$, $R^3$, $R^4$, X and Y are defined above, R is hydrogen, $R^7$ is $C_1$–$C_4$ alkyl or both $R^7$'s taken together are ethylene or propylene and A is oxygen or sulfur is prepared from the appropriately substituted aryl aldehyde utilizing the standard Hantzsch reaction conditions. The aryl dihydropyridine (1) wherein R is other than hydrogen is obtained by standard alkylation procedures employing the appropriate alkylating agent, such as alkyl halide, alkyl sulfate, benzyl halide or alkyl haloformate.

The aryl dihydropyridine compound (1) may be treated under mild acidic conditions to remove the acetal or thioacetal protecting group and yield the aryl dihydropyridine (2). Mercuric salts may also be employed to remove the thioacetal protecting group.

The aryl dihydropyridine compound (2) is then treated at −10° to 50° C., preferably ambient temperature, with between 0.5 and 5.0 equivalents, preferably 1.0 equivalent, of p-toluenesulfonylhydrazine (TsNHNH₂) in an inert solvent to yield the aryl dihydropyridine (3). The aryl dihydropyridine (3), without isolation or after isolation, is heated at 75° to 125° C. either in an inert solvent or neat to afford the compound of the formula (I). Exemplifying the inert solvents which may be utilized in the cyclization reaction are aromatic hydrocarbons, such as benzene and toluene. This is the best mode for the preparation of the compounds of the formula (I).

As indicated above, the compounds of this invention are useful as calcium channel blockers, and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory system; (vi) useful antihypercholesterolemic and antilipademic action; (vii) protection of the ischemic myocardium; (viii) inhibition of irritable bowel syndrome and esophageal spasm; and, (ix) inhibition of migraine. Some of these compounds are also useful cardiotonic agents.

The representative compounds of the present invention were found to inhibit vascular calcium contraction, reduce cardiac contractile force, inhibit calcium-mediated tracheal contraction, inhibit calcium uptake in pituitary cells, or displace tritiated nitrendipine from membrane.

The compounds of the present invention can be administered in any suitable form; e.g. orally, sublingually, transdermally, or parenterally; i.e. intravenously, interperitoneally, etc. Thus, the compounds can be offered in a form (a) for oral administration e.g. as tablets in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., nitroglycerine tablets, lactose tablets, and the like, for rapid dissolution or high molecular weight methylcellulose tablets, carboxymethylcellulose tablets, and the like, for slower, time-releasing delivery; or, (c) for parenteral administration e.g. dissolved or dispersed in a suitable liquid carrier or emulsified.

The pharmaceutical preparations thus described are made following the conventional techniques of the pharmaceutical chemist as appropriate to the desired end product.

The ratio of active compound to compounding ingredients i.e. carrier, diluent etc. will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or β-blocking agents. For example, the compounds of this invention can be given in combination with such compounds as enalapril, hydralazine hydrochloride, hydrochlorothiazide, methyldopa, timolol, and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

The following Examples are provided to further illustrate the best mode currently known for preparing the compounds and compositions of this invention, but are not to be construed as limiting this invention in any manner.

EXAMPLE 1

Preparation of Dimethyl 1,2,3,6α-tetrahydro-2,4-dimethyl-1,2,6-metheno-3-benzazocine-5,11α-dicarboxylate A solution of dimethyl 2,6-dimethyl-4-(2-formylphenyl)-1,4-dihydropyridine-3,5-dicarboxylate (1.0 g, 3.0 mmol) and recrystallized p-toluenesulfonylhydrazine (0.60 g, 3.2 mmol) in benzene (100 mL) was stirred at room temperature for one hour. The precipitate that formed was removed by filtration, added to fresh benzene (100 mL) and the solution was stirred and refluxed for one hour. The cooled solution was washed with a dilute solution of sodium bicarbonate, water and brine, was dried over anhydrous magnesium sulfate, filtered, and was evaporated to dryness. The resulting residue was then purified by flash chromatography (silica gel, 35% ethyl acetate in hexane) to afford the title compound. Recrystallization of this material from ethyl acetate-hexane gave the title compound; m.p. 162°–163.5° C.; IR 3280 (NH); 1720 (CO) cm$^{-1}$; $^1$H NMR $\delta$1.63 (s, 3H, $C_2$—$CH_3$), 2.18 (s, 3H, $C_4$—$CH_3$), 2.76 (s, 1H, $C_1$—H), 3.74 (s, 3H, $OCH_3$), 3.82 (s, 3H, $OCH_3$), 4.16 (s, 1H, NH), 5.25 (s, 1H, $C_6$—H), 7.06–7.16 (m, 4H, ArH).

Anal. Calcd. for $C_{18}H_{19}NO_4$: C, 68.99; H, 6.11; N, 4.47; Found: C, 69.16; H, 6.30; N, 4.36.

EXAMPLE 2

Preparation of Dimethyl 1,2,3,6α-tetrahydro-2,4-dimethyl-9-methoxy-1,2,6-metheno-3-benzazocine-5,11α-dicarboxylate (a) Dimethyl 1,4,5,8-tetrahydro-11-methoxy-4,6-dimethyl-1,4,8-metheno-2,3,5-benzotriazocine-7,13α-dicarboxylate (2a)

A solution of dimethyl 2,6-dimethyl-4-(2-formyl-4-methoxyphenyl)-1,4-dihydropyridine-3,5-dicarboxylate (0.36 g, 1.0 mmol) and recrystallized p-toluenesulfonylhydrazine (0.20 g, 1.0 mmol) in benzene (20 mL) was stirred at room temperature for one hour. The solvent was removed under vacuum, and the product was purified by flash chromatography (silica gel; 35% ethyl acetate in hexane), followed by dissolving the residue in cold ethyl acetate and by initiating crystallization by the addition of hexane to afford pure crystalline Compound 2a; m.p. 125° C. (with gas evolution); IR 3330 (NH), 1730, 1700 (CO) cm$^{-1}$; $^1$H NMR $\delta$1.57 (s, 3H, $C_4$—$CH_3$), 2.30 (s, 3H, $C_6$—$CH_3$), 3.75 (s, 3H, $OCH_3$), 3.82 (s, 3H, $OCH_3$), 3.83 (s, 3H, $OCH_3$), 4.75 (s, 1H, $C_8$—H), 4.78 (s, 1H, NH), 6.82 (d,d, 1H, $C_{10}$—H), 6.83 (s, 1H, $C_1$—H), 7.08 (d, 1H, $C_9$—H), 7.14 (d, 1H, $C_{12}$—H).

Anal. Calcd. for $C_{19}H_{21}N_3O_5$: C, 61.44; H, 5.70; N, 11.32; Found: C, 61.47; H, 5.90; N, 11.49.

(b) Dimethyl 1,2,3,6α-tetrahydro-2,4-dimethyl-9-methoxy-1,2,6-metheno-3-benzazocine-5,11α-dicarboxylate A solution of dimethyl 2,6-dimethyl-4-(2-formyl-4-methoxyphenyl)-1,4-dihydropyridine-3,5-dicarboxylate (1.26 g, 3.5 mmol) and recrystallized p-toluenesulfonylhydrazine (0.69 g, 3.7 mmol) in benzene (50 mL) was stirred at room temperature for one hour. During this time, a solid crystallized from solution, but then quickly redissolved. The solution then was refluxed for one hour. The benzene solution was washed with water, brine, dried over anhydrous magnesium sulfate, filtered, and concentrated to dryness. The residue was purified by flash chromatography (silica gel, 35% ethyl acetate in hexane) followed by recrystallization from ethyl acetate-hexane to afford the title compound; m.p. 160.5°–162° C.; IR 3320 (NH), 1730 (CO) cm$^{-1}$; $^1$H NMR $\delta$1.63 (s, 1H, $C_2$—$CH_3$), 2.18 (s, 3H, $C_4$—$CH_3$), 2.70 (s, 1H, $C_1$—H), 3.74 (s, 3H, $OCH_3$), 3.76 (s, 3H, ArOCH$_3$), 3.80 (s, 3H, $OCH_3$), 4.18 (s, 1H, NH), 5.16 (s, 1H, $C_6$—H), 6.6–7.0 (m, 3H, ArH).

Anal. Calcd. for $C_{19}H_{21}NO_5$: C, 66.46; H, 6.17; N, 4.08; Found: C, 66.50; H, 6.38; N, 3.97.

Alternatively, a sample of the Compound 2a was melted at 125° C. in an oil bath. The residue was chromatographically identical to the title compound prepared by the above procedure.

EXAMPLE 3

Preparation of Dimethyl 1,2,3,6α-tetrahydro-2,4-dimethyl-8-nitro-1,2,6-metheno-3-benzazocine-5,11α-dicarboxylate (a) 3-Hydroxy-6-nitro-1(3H)-isobenzofuranone (3a)

A mixture of 6-nitro-1(3H)-isobenzofuranone (8.99 g, 50.0 mmol) and N-bromosuccinimide (8.9 g, 50.0 mmol) in carbon tetrachloride (135 mL) was stirred and heated under reflux for one hour during which time the reaction mixture was exposed to the light from a 275 Watt, 125 Volt Hanovia sunlamp that was situated 8 inches from the flask. After cooling, the succinimide was removed by filtration, and the filtrate was evaporated in vacuo. The oily residue was mixed with water (200 mL), and the mixture was refluxed for one hour to give a clear, colorless solution. On cooling, the Compound 3a crystallized from solution. An analytical sample was prepared by recrystallization from water; m.p. 157°–160° C.; IR 3390 cm$^{-1}$ (OH), 1770 cm$^{-1}$ (C=O), $^1$H NMR (CDCl$_3$-Me$_2$SO-d$_6$-D$_2$O) $\delta$6.78 (s, br, 1H, H$_3$), 7.88 (d, 1H, H$_4$, $J_{4,5}$=9 Hz), 8.56 (d, 1H, H$_5$, J=9 Hz), 8.62 (s, 1H, H$_6$).

Anal. Calcd. for $C_8H_5NO_5$: C, 49.24; H, 2.58; N, 7.18; Found: C, 49.39; H, 2.58; N, 7.13.

(b) 2-[1,3-Dithian-2-yl]-5-nitrobenzoic acid (3b)

To an ice-cooled mixture of the Compound 3a (5.00 g, 25.6 mmol) and propane-1,3-dithiol (2.92 g, 27 mmol) in chloroform (75 mL) was added boron trifluoride etherate (2 mL). The mixture was stirred and allowed to warm to room temperature. After stirring for 3 hours, most of the solid had dissolved. Magnesium sulfate was added to dry the solution, and stirring was continued overnight. Filtration and evaporation of the solvent afforded a light yellow solid. This material was triturated with butyl chloride to give the Compound 3b; m.p. 192°–194° C.; 1H NMR (CDCl$_3$+MeSO-d$_6$+D$_2$O) δ1.8–2.3 (m, 2H, CH$_2$CH$_2$CH$_2$), 2.9–3.2 (m, 4H, —CH$_2$CH$_2$CH$_2$—), 6.56 (s, 1H, —SCHS—), 7.6–8.8 (m, 3H, ArH).

Anal. Calcd. for C$_{11}$H$_{11}$NO$_4$S$_2$: C, 46.30; H, 3.89; N, 4.91; Found: C, 46.29; H, 3.84; N, 5.03.

(c) 2-[1,3-Dithian-2-yl]-5-nitrobenzyl alcohol (3c)

To an ice cooled, stirred solution of the Compound 3b (5.00 g, 17.5 mmol) in tetrahydrofuran (100 mL) was added dropwise over 30 minutes 1.0M BH$_3$.THF (20 mL). The solution was allowed to warm to room temperature and was stirred overnight. Additional 1.0M BH$_3$.THF (5 mL) was added, and the solution was stirred another 4 hours. Water was added to hydrolyze the reaction, and the solution then was evaporated to dryness. The residue was dissolved in diethyl ether, and this solution was washed with a saturated solution of sodium carbonate, brine, and was dried over anhydrous magnesium sulfate. Evaporation of the solvent and recrystallization of the product from acetonitrile afforded the Compound 3c; m.p. 130°–131° C.; IR 3600 cm$^{-1}$ (OH); 1H NMR (CDCl$_3$+D$_2$O) δ1.8–2.2 (m, 2H, —CH$_2$CH$_2$CH$_2$—), 2.8–3.2 (m, 4H, —CH$_2$CH$_2$CH$_2$—), 4.61 (s, 2H, CH$_2$O), 5.48 (s, 1H, SCHS), 7.7–8.3 (m, 3H, ArH).

Anal. Calcd. for C$_{11}$H$_{13}$NO$_3$S$_2$: C, 48.69; H, 4.83; N, 5.16; Found: C, 49.03; H, 5.01; N, 5.01.

(d) 2-[1,3-Dithian-2-yl]-5-nitrobenzaldehyde (3d)

To a solution of 3.47 g (12.8 mmol) of the Compound 3c in methylene chloride (100 mL) was added pyridinium chlorochromate (4.15 g, 19.2 mmol). The mixture was stirred for one hour, an additional pyridinium chlorochromate (2.0 g) was added, and the mixture was stirred 15 hours. Diethyl ether (200 mL) was added to the reaction mixture, and the solvent was decanted and evaporated. The residue was purified by chromatography (silica gel, chloroform) to afford the Compound 3d as light yellow crystals; m.p. 99°–101° C.; IR 1730 cm$^{-1}$ (C=O); 1H NMR δ1.7–2.3 (m,2H, —CH$_2$CH$_2$CH$_2$—), 2.8–3.3 (m, 4H,—CH$_2$CH$_2$CH$_2$—), 6.13(s, 1H, —SCHS—), 7.8–8.7 (m, 3H, ArH), 10.45 (s, 1H,CHO).

Anal. Calc. for C$_{11}$H$_{11}$NO$_3$S$_2$: C, 49.05; H, 4.12; N, 5.20; Found: C, 49.16; H, 4.18; N, 5.60.

(e) Dimethyl 4-(2-[1 3-dithian-2-yl]-5-nitro)phenyl-2,6-dimethyl-1,4-dihydropyridine-3,5-dicarboxylate (3e)

To a solution of the Compound 3d (2.27 g, 8.43 mmol) in methanol (25 mL) was added methyl acetoacetate (0.99 g, 8.5 mmol) and methyl-β-aminocrotonate (0.99 g, 8.5 mmol). The solution was stirred and refluxed for 24 hours. The crystalline solid that formed during the reflux period was removed by filtration, and was washed with methanol and dried to afford the Compound 3e; m.p. 278°–279° C.; IR 3435 cm$^{-1}$ (NH), 1695 cm$^{-1}$ (CO); 1H NMR δ1.9–2.3 (m, 2H, —CH$_2$CH$_2$CH$_2$—), 2.37 (s, 6H, CH$_3$), 2.8–3.3 (m, 4H, —CH$_2$CH$_2$CH$_2$—), 3.64 (s, 6H, OCH$_3$), 5.39 (s, 1H, C$_4$—H), 5.86 (s, 1H, —SCHS—), 5.92 (s, 1H, NH), 7.8–8.2 (m, 3H, ArH).

Anal. Calcd. for C$_{21}$H$_{24}$N$_2$O$_6$S$_2$: C, 54.29; H, 5.21; N, 6.03; Found: C, 54.20; H, 5.25; N, 6.13.

(f) Dimethyl 4-(2-Formyl-5-nitro)phenyl-2,6-dimethyl-1,4-dihydropyridine-3,5-dicarboxylate (3f)

To a vigorously stirred mixture of mercuric oxide (0.93 g, 4.3 mmol) and boron trifluoride etherate (0.612 g, 4.31 mmol) in 15% aqueous tetrahydrofuran (10 mL) was added dropwise over 10 minutes, a solution of the Compound 3e (1.00 g, 2.15 mmol) in tetrahydrofuran (35 mL). The mixture was stirred for 18 hours at room temperature and then was refluxed for 15 minutes. The mixture was concentrated to dryness and chloroform was added to the residue. The mixture was filtered, and the filtrate was washed with a sodium carbonate solution, water, and was dried over anhydrous magnesium sulfate. Evaporation of the solvent afforded the Compound 3f. An analytical sample of the Compound 3f was prepared by flash chromatography (silica gel, 35% ethyl acetate-hexane), followed by recrystallization from ethyl acetate hexane; m.p. 233°–236° C.; IR 3375 (NH), 1710, 1690, 1645 (CO) cm$^{-1}$, 1H NMR δ2.40 (s, 6H, CH$_3$), 3.56 (s, 6H, OCH$_3$), 5.83 (s, 1H, C$_4$-H), 6.00 (s, 1H, NH), 7.7–8.3 (m, 3H, ArH), 10.65 (s, 1H, CHO).

Anal. Calcd. for C$_{18}$H$_{18}$N$_2$O$_7$: C, 57.75; H, 4.84; N, 7.49; Found: C, 57.90; H, 4.88; N, 7.57.

(g) Dimethyl 1,2,3,6α-tetrahydro-2,4-dimethyl-8-nitro-1,2,6-metheno-3-benzazocine-5,11α-dicarboxylate (3g)

To a solution of the Compound 3f (0.8 g, 2.14 mmol) in benzene (50 mL) was added recrystallized p-toluenesulfonylhydrazine (0.418 g, 2.24 mmol). The solution was stirred under nitrogen at room temperature. After about 30 minutes, a crystalline precipitate formed. After stirring another 45 minutes, a homogeneous solution was obtained. The solution then was stirred for an additional 2 hours at room temperature, and for 16 hours at reflux. The solvent was removed and the residue was purified by flash chromatography (silica gel, 30% ethyl acetate in hexane), followed by recrystallization from ethyl acetate-hexane, to afford pure title compound; m.p. 177°–179° C.; IR 3310 (NH), 1710, 1640 (CO) cm$^{-1}$; 1H NMR δ1.68 (s, 3H,C$_2$—CH$_3$), 2.19 (s, 3H,—C$_4$—CH$_3$), 2.80 (s, 1H, C$_1$—H),3.77 (s, 3H,—OCH$_3$), 3.85 (s, 3H, OCH$_3$), 4.21 (s, 1H, NH), 5.35 (s, 1H, C$_6$—H), 7.8–8.1 (m, 3H, ArH).

Anal. Calcd. for C$_{18}$H$_{18}$N$_2$O$_6$: C, 60.33; H, 5.06; N, 7.82; Found: C, 60.48; H, 5.06; N, 7.96.

EXAMPLE 4

Preparation of Trimethyl 1,2,3,6α-tetrahydro-2,4-dimethyl-1,2,6-metheno-3-benzazocine-3,5,11α-tricarboxylate (a) Trimethyl 2,6-dimethyl-4-(2-[2-(1,3-dioxolanyl)])phenyl-1,4-dihydropyridine-1,3,5-tricarboxylate (4a)

To a suspension of sodium hydride (61% NaH in mineral oil) (0.393 g) in tetrahydrofuran (80 mL) was added dropwise, while stirring magnetically a solution of dimethyl 2,6-dimethyl-4-(2-[2-(1,3-dioxolanyl)]-phenyl)-1,4-dihydropyridine-3,5-dicarboxylate (3.73 g, 10 mmol) in a mixture of tetrahydrofuran (35 mL) and dimethylformamide (8 mL). After the addition was completed, the mixture was refluxed for 15 minutes, and then was cooled to room temperature. Methyl chloroformate (0.945 g, 10 mmol) was added and the mixture was refluxed for 18 hours. The reaction mixture was concentrated under vacuum and the residue was dissolved in ethyl acetate. This solution was washed with water (5×100 mL), brine, dried over anhydrous magnesium sulfate, and concentrated to dryness. The resulting residue was purified by chromatography (silica gel, eluting with 30% ethyl acetate in hexane) to afford the Compound 4a. An analytical sample was prepared by recrystallization from ethyl acetate-hexane; m.p. 120.5° C.; $^1$H NMR $\delta$2.47 (s, 6H, CH$_3$), 3.73 (s, 6H, OCH$_3$), 3.83 (s, 3H, NCO$_2$CH$_3$), 4.03–4.24 (m, 4H, —OCH$_2$CH$_2$O—), 5.47 (s, 1H, C$_4$—H), 6.26 (s, 1H, OCHO), 6.97–7.6 (m, 4H, ArH).

Anal. Calcd. for C$_{22}$H$_{25}$NO$_8$: C, 61.24; H, 5.84; N, 3.25; Found: C, 61.02; H, 5.99; N, 3.36.

(b)
Trimethyl-2,6-dimethyl-4-(2-[(2-[4-methylphenyl]sulfonyl hydrazono)methyl])phenyl-1,3,5-(4H)-pyridinetricarboxylate (4b)

A solution of the Compound 4a (1.15 g, 2.67 mmol) in acetone (100 mL) containing a catalytic amount of p-toluenesulfonic acid monohydrate was stirred at room temperature for 2.5 hours. The solution was concentrated under vacuum and the residue was redissolved in methylene chloride. After washing with a dilute solution of sodium bicarbonate, water, and brine, the solution was dried over anhydrous magnesium sulfate, filtered and concentrated to dryness. The residue was purified by flash chromatography on silica gel. Elution with 50% ethyl acetate-hexane afforded trimethyl 2,6-dimethyl-4-(2-formylphenyl)-1,4-dihydropyridine-1,3,5-tricarboxylate, which was characterized by its NMR spectrum: $^1$H NMR $\delta$2.54 (s, 6H, CH$_3$), 3.68 (s, 6H, OCH$_3$), 3.90 (s, 3H, NCO$_2$CH$_3$), 5.89 (s, 1H, C$_4$—H), 7.1–7.9 (m, 4H, ArH), 10.69 (s, 1H, CHO). A solution of 1.70 g (0.0044 mol) of this material and recrystallized p-toluenesulfonylhydrazine (0.819 g, 4.4 mmol) benzene (75 mL) was stirred at room temperature for 1.5 hours. The solvent was evaporated. The residue was purified by flash chromatography (silica gel, 35% ethyl acetate in hexane) to afford the Compound 4b; m.p. 125°–126° C.; IR 3200 (NH), 1715 (CO) cm$^{-1}$; $^1$H NMR $\delta$2.42 (s, 3H, ArCH$_3$), 2.46 (s, 6H, CH$_3$), 3.59 (s, 6H, OCH$_3$), 3.85 (s, 3H, NCO$_2$CH$_3$), 5.58 (s, 1H, C$_4$—H), 6.9–8.5 (m, 8H, ArH).

Anal. Calcd. for C$_{27}$H$_{29}$N$_3$O$_8$S: C, 58.37; H, 5.26; N, 7.56; Found: C, 58.70; H, 5.53; N, 7.56.

(c)
Trimethyl-1,2,3,6$\alpha$-tetrahydro-2,4-dimethyl-1,2,6-metheno-3-benzazocine-3,5,11$\alpha$-tricarboxylate (4c)

A solution of the Compound 4b (1.1 g, 2.0 mmol) in benzene (100 mL) was refluxed for 2 hours. The solution was evaporated to dryness, and the residue was purified by flash chromatography (silica gel, 30% ethyl acetate in hexane) to afford the title compound; m.p. 99°–100° C.; IR 1700–1750 cm$^{-1}$ (CO); $^1$H NMR $\delta$1.68 (s, 3H, C$_2$—CH$_3$), 2.33 (s, 3H, C$_4$—CH$_3$), 3.19 (s, 1H, C$_1$—H), 3.38 (s, 3H, 11$\alpha$—CO$_2$CH$_3$), 3.74 (s, 3H, OCH$_3$), 3.90 (s, 3H, OCH$_3$), 5.04 (s, 1H, C$_6$—H), 7.0–7.2 (m, 4H, ArH).

Anal. Calcd. for C$_{20}$H$_{21}$NO$_6$: C, 64.68; H, 5.70; N, 3.77; Found: C, 64.92; H, 5.80; N, 3.42.

EXAMPLE 5

Alternate preparation of Dimethyl 1,2,3,6$\alpha$-tetrahydro-2,4-dimethyl-1,2,6-metheno-3-benzazocine-5,11$\alpha$-dicarboxylate A solution of the Compound 4b (0.111 g 0.2 mmol) and potassium hydroxide (0.014 g, 0.25 mmol) in methanol (10 mL) containing water (0.5 mL) was stirred at room temperature overnight. After evaporation to dryness, the residue was taken up in methylene chloride, washed with water, dried sodium sulfate, and evaporated to dryness. The residue was dissolved in benzene (20 mL), and was refluxed for 2 hours. The solution was evaporated to dryness, and the residue was purified by flash chromatography (silica gel, 20% ethyl acetate in hexane). The residue was chromatographically and spectrally identical to the compound prepared by the direct reaction of p-toluenesulfonylhydrazine with dimethyl-2,6-dimethyl-4-(2-formyl)-phenyl-1,4-dihydropyridine-3,5-dicarboxylate according to Example 1.

EXAMPLES 6–21

Utilizing the general procedure of Examples 1, 2 or 3 and starting with appropriately substituted aryl dihydropyridines the following compounds of the formula (I) are prepared.

| Compound | R | R$^1$ | R$^2$ | R$^3$ | R$^4$ | X | Y |
| --- | --- | --- | --- | --- | --- | --- | --- |
| 6 | H | Et | Et | Et | Et | H | H |
| 7 | H | H | Me | Me | Et | H | 9-OMe |
| 8 | Me | Me | —CH$_2$CH(OH)—CH$_2$OH | Me | Me | H | H |
| 9 | PhCH$_2$ | Me | Et | Et | Me | H | 9-NO$_2$ |
| 10 | H | Me | Me | —CH$_2$CH$_2$OCH$_3$ | Me | H | 7-CF$_3$ |
| 11 | CO$_2$Me | Me | 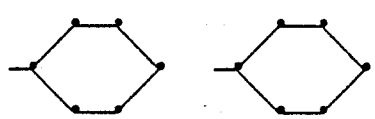 | 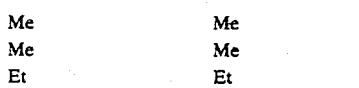 | Me | H | H |
| 12 | CO$_2$Et | Me | Me | Me | Me | H | H |
| 13 | H | —CH$_2$CH=CH$_2$ | Me | Me | Me | 8-Cl | 9-Cl |
| 14 | H | —CH$_2$OH | Et | Et | Me | H | H |

-continued

| Compound | R | R¹ | R² | R³ | R⁴ | X | Y |
|---|---|---|---|---|---|---|---|
| 15 | H | 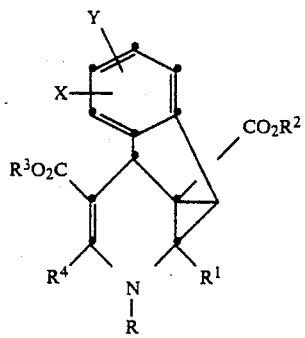 | Me | Me | Me | 8-OMe | H |
| 16 | Et | Me | —CH₂CH=CH₂ | —CH₂CH=CH₂ | Me | H | 8-Me |
| 17 | H | Me | —CH₂CH₂OH | Me | Me | H | 7-Cl |
| 18 | PhCH₂ | Me | Me | —CH₂CH₂OCH₂CH₂OCH₃ | Me | H | H |
| 19 | H | Me | —CH₂CH₂NMe₂ | —CH₂CH₂NMe₂ | Me | H | 8-CF₃ |
| 20 | H | Me | —CH₂N(CH₃)CH₂Ph | Et | Me | 7-CN | H |
| 21 | H | Me | 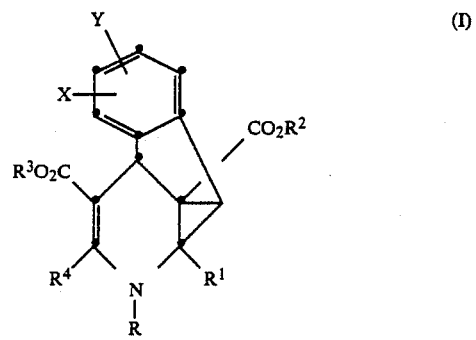 | | Me | H | H |

It should be noted that for the preparation of Compounds 8, 14 and 17 the hydroxyalkyl moiety is acylated with acetic anhydride prior to cyclization and then deacylated with sodium hydroxide.

EXAMPLE 21

As a specific embodiment of a composition of this invention an active ingredient, such as dimethyl 1,2,3,6α-tetrahydro-2,4-dimethyl-1,2,6-metheno-3-benzazocine-5,11α-dicarboxylate, is formulated to yield 5000 compressed tablets, each containing 50 mg of the active ingredient, as follows:

| | | |
|---|---|---|
| Active ingredient | 250 | grams |
| Starch | 70 | grams |
| Dibasic calcium phosphate hydrous | 500 | grams |
| Calcium stearate | 2.5 | grams |

What is claimed is:

1. A compound represented by the following general structural formula (I):

(I)

wherein:
R is hydrogen, $C_1$–$C_8$ alkyl, benzyl or $C_1$–$C_4$ carboalkoxy;
$R^1$ and $R^4$ independently are hydrogen, $C_1$–$C_8$ alkyl, $C_2$–$C_8$ alkenyl, $C_3$–$C_8$ cycloalkyl or $C_1$–$C_8$ hydroxyalkyl;
$R^2$ and $R^3$ independently are $C_1$–$C_8$ alkyl, $C_2$–$C_8$ alkenyl, $C_3$–$C_8$ cycloalkyl, $C_1$–$C_8$ hydroxyalkyl, $C_1$–$C_8$ dihydroxyalkyl, $C_2$–$C_8$ alkoxyalkyl, $C_3$–$C_8$ alkoxy(alkoxyalkyl) or $C_1$–$C_8$ aminoalkyl wherein the amino group is $NR^5R^6$ in which $R^5$ and $R^6$ independently are hydrogen, $C_1$–$C_8$ alkyl, $C_7$–$C_{14}$ phenylalkyl or $R^5$ and $R^6$ together with the N atom form a 5 or 6 membered heterocycle selected from the group consisting of piperidinyl, morpholinyl, thiomorpholinyl, pyrrolidinyl, piperazinyl or N′-$C_1$–$C_4$-alkylpiperazinyl; and
X and Y independently are hydrogen, $C_1$–$C_8$ alkyl, $C_1$–$C_8$ alkoxy, $CF_3$, cyano, nitro or halo, or X and Y together with the phenyl group to which they are attached form a naphthyl or benzoxadiazole group,
or a pharmaceutically acceptable salt thereof.

2. A compound represented by the following general structure formula (I):

(I)

wherein
R is hydrogen, $C_1$–$C_8$ alkyl or $C_1$–$C_4$ carboalkoxy;
$R^1$ and $R^4$ independently are hydrogen or $C_1$–$C_8$ alkyl;
$R^2$ and $R^3$ independently are $C_1$–$C_8$ alkyl or $C_1$–$C_8$ aminoalkyl wherein the amino group is $NR^5R^6$ in which $R^5$ and $R^6$ independently are hydrogen, $C_1$–$C_8$ alkyl or $C_7$–$C_{14}$ phenylalkyl; and
X and Y independently are hydrogen, $C_1$–$C_8$ alkyl, $C_1$–$C_8$ alkoxy, $CF_3$, cyano, nitro or halo.

3. A compound of claim 2 wherein: R is hydrogen; $R^1$, $R^2$, $R^3$ and $R^4$ independently are $C_1$–$C_8$ alkyl; and X and Y independently are hydrogen, nitro or $C_1$–$C_8$ alkoxy and are in the 8-and 9 positions respectively.

4. A compound of claim 3 which is dimethyl 1,2,3,6α-tetrahydro-2,4-dimethyl-1,2,6-metheno-3-benzazocine-5,11α-dicarboxylate.

5. A compound of claim 3 which is dimethyl 1,2,3,6α-tetrahydro-2,4-dimethyl-1,2,6-metheno-9-methoxy-3-benzazocine-5,11α-dicarboxylate.

6. A compound of claim 3 which is dimethyl 1,2,3,6α-tetrahydro-2,4-dimethyl-1,2,6-metheno-8-nitro-3-benzazocine-5,11α-dicarboxylate.

7. A compound of claim 2 which is trimethyl 1,2,3,6α-tetrahydro-2,4-dimethyl-1,2,6-metheno-3-benzazocine-3,5,11α-tricarboxylate.

8. A pharmaceutical composition, useful in the treatment of cardiovascular disorders comprising a nontoxic therapeutically effective amount of a compound according to claim 1 in an admixture with a pharmaceutically acceptable carrier.

9. A method of treatment for cardiovascular disorders which comprises administering to a subject in need of such of such treatment a nontoxic therapeutically effective amount of a compound according to claim 1.

* * * * *